United States Patent
Zhou et al.

(10) Patent No.: US 6,624,883 B1
(45) Date of Patent: Sep. 23, 2003

(54) METHOD OF AND APPARATUS FOR DETERMINING WOOD GRAIN ORIENTATION

(75) Inventors: Jianqin Zhou, Vancouver (CA); Jun Shen, Richmond (CA)

(73) Assignee: National Research Council of Canada, Ottawa (CA)

( * ) Notice: Subject to any disclaimer, the term of this patent is extended or adjusted under 35 U.S.C. 154(b) by 231 days.

(21) Appl. No.: 09/670,388

(22) Filed: Sep. 28, 2000

(51) Int. Cl.[7] .............................................. G01N 21/00
(52) U.S. Cl. .............................. 356/237.1; 250/559.25; 250/563; 364/507
(58) Field of Search .......................... 356/237.1, 237.2, 356/237.4, 238.1, 238.2, 238.3, 239.7, 239.8, 364–369; 250/559.25, 559.05, 559.08, 563; 324/58.5 R; 364/507

(56) References Cited

U.S. PATENT DOCUMENTS

| | | | |
|---|---|---|---|
| 3,805,156 A | | 4/1974 | Norton et al. ............ 324/61 R |
| 3,976,384 A | | 8/1976 | Matthews et al. .......... 356/200 |
| 4,221,974 A | * | 9/1980 | Mueller et al. ............ 250/563 |
| 4,482,250 A | * | 11/1984 | Hirvonen et al. ........... 356/369 |
| 4,500,835 A | * | 2/1985 | Heikkila ................ 324/58.5 R |
| 4,606,645 A | | 8/1986 | Matthews et al. .......... 356/446 |
| 4,764,017 A | * | 8/1988 | Hirvone ..................... 356/369 |
| 4,916,629 A | | 4/1990 | Bogue et al. ............... 364/507 |
| 4,931,657 A | * | 6/1990 | Houston et al. ............ 356/369 |
| 4,984,172 A | * | 1/1991 | Luminari .................... 250/563 |
| 5,023,805 A | * | 6/1991 | Aune et al. .................. 364/507 |
| 5,252,836 A | | 10/1993 | Matthews et al. .......... 250/571 |
| 5,257,101 A | * | 10/1993 | Lee ............................. 358/101 |
| 5,412,220 A | | 5/1995 | Moore ........................ 250/563 |
| 5,644,392 A | | 7/1997 | Soest et al. .................. 356/237 |
| 5,703,960 A | | 12/1997 | Soest .......................... 382/141 |
| 5,960,104 A | * | 9/1999 | Conners et al. ............. 382/141 |
| 6,449,036 B1 | * | 9/2002 | Wollmann et al. ....... 356/237.2 |

FOREIGN PATENT DOCUMENTS

GB      2 285 861     *   7/1995

OTHER PUBLICATIONS

2nd International Conference on Scanning Technology in Sawmilling, Oct. 1–2, 1987.
1) Matthews, "Wood, Light and Objective Scanning" XI1–XI13.
2) Soest, "Applications of Optical Measurements of Slope of Grain" XII1–XII10.
3) Conners, et al. "A Computer Vision System for Grading Hardwood Lumber" XV1–XV7.
4) Godinez, "Automated Optical Inspection of Wood Grain Patterns and Defects" XVI1–XVI5.

* cited by examiner

*Primary Examiner*—Frank G. Font
*Assistant Examiner*—Sang H. Nguyen (57) ABSTRACT

A laser scanning system for determining wood grain orientation has been developed. The system employs a polarizer for separating the emergent laser light from the reflected laser light to decrease the laser image noise, a variable voltage source for intensifying the emergent laser light to increase the laser image signal, and an algorithm of phase demodulation for signal transformation, phase demodulation, and contrast feedback to further improve the signal-to-noise ratio of the laser images. The system is capable of extracting wood grain orientation quickly and precisely from the laser images with low signal-to-noise ratio, such as the images on the surfaces of hardwood species and roughsawn materials.

32 Claims, 6 Drawing Sheets

METHOD OF AND APPARATUS FOR DETERMINING WOOD GRAIN ORIENTATION

BACKGROUND OF THE INVENTION

1. Field of the Invention

The present invention relates methods of and apparatus for determining wood grain orientation for use, for example, in lumber grading, defect inspection and quality control.

2. Description of the Related Art

The detection of wood grain orientation is normally carried out by human observation and decision. However, modem forest industry requires scanning technology to measure wood grain orientation automatically, reliably and precisely.

Wood is generally regarded as an orthogonal anisotropic material. The anatomic anisotropy of wood cells gives rise to a grain structure with a grain orientation determined by longitudinal axes of the wood cells. The interaction of wood materials with various types of radiation brings about an anisotropic distribution of the radiation, which can be used as an indication of the wood grain orientation.

Based on the anisotropic distribution of the dielectric constant of wood materials, a slope-of-grain indicator (SGI) has been developed to determine the grain orientation of softwood and hardwood species. For this purpose, a transducer with capacitor plates is mounted in close proximity to a wood surface and rotated for dielectric constant scanning and sensing. When the direction of an electric field applied to the capacitor plates is parallel to the wood grain orientation, the transducer capacitance, which is proportional to the wood dielectric constant, reaches its maximum. The resolution of the SGI depends on the transducer diameter (¾ or 1⅜ inch). The speed could be up to 3600 rpm. The precision might approach ±1°, provided the transducer-to-wood distance is maintained within a prescribed limit (⅛ or ¼ inch).

However, when SGI is employed, the measurement of the grain orientation is not independent of the gradients of wood moisture and density. SGI is also sensitive to the transducer-to-wood distance, unless the distance is maintained within the above prescribed limit, resulting in close-contact measurement with less flexibility.

Based on the attenuation, phase shift and depolarization of a polarized microwave transmitted through wood, a microwave transmission method has been suggested to probe the amplitude, phase and polarization of a microwave field and to measure the moisture, density and grain orientation of wood materials. Approximately, the attenuation reflects moisture, the phase shift reflects both moisture and density, and the depolarization reflects grain orientation. This method was improved to cope with the dependence of depolarization on moisture and density, which makes grain orientation prediction rather complicated. The experimental data show that the method can measure the grain orientation reliably up to 30° at a speed up to 40 kHz and a resolution about 2 cm.

It is, however, a disadvantage of the microwave transmission method that calibrations are complicated because of a considerable interaction between the parameters. The grain orientation can be deduced reliably only when the specimen thickness and moisture are great enough to introduce sufficient dielectric anisotropy to appreciably depolarize the incident wave. The apparatus and techniques are very complex, although the principles and experiments show the method to be feasible for on-line lumber grading by recording moisture, density and grain orientation in real time.

Instead of employing human observation and decision, a scanning system consisting of a camera and a computer for pattern recognition has been used to detect wood defects. This system can be used to determine wood grain orientation based on wood splits, seasoning checks, and mainly demarcations between earlywood and latewood. The precision and speed depend on the algorithms designed for pattern recognition.

However, this scanning system for pattern recognition, which is time consuming, may not give correct grain orientation because the demarcations between earlywood and latewood, especially in the case of flatsawn surfaces, are not reliable indicators of grain orientation.

Several scanning systems based on the interaction of wood materials with laser light have been proposed to detect wood grain orientation. When a laser light strikes a wood surface, the laser light is split into two parts: a reflected light bouncing off the wood surface and a transmitted light propagated in the wood material, which is an anisotropic absorbing medium. Light propagated across wood cell walls will be attenuated more than light propagated along wood cell lumens, where the attenuation constant of air or water is almost zero. In the process of propagation, some of the transmitted light will emerge from the wood surface, forming an elongate laser spot having its major axis along the grain orientation as a result of the highly directional propagation beneath the wood surface. Therefore, the light on the wood surface is a mixture of emergent laser light, reflected laser light, and non-laser illumination.

The shape of the reflected laser spot is affected by wood surface qualities (planed, sanded, or sawn). Generally, a roughsawn surface will cause more jagged edges on the reflected laser spot than other wood surfaces. The elongate emergent laser spot (caused by wood cell structure) is mixed with the jagged reflected laser spot (caused by wood surface roughness), bringing about the inaccurate information of wood grain orientation.

The shape of the emergent laser spot is affected by wood species. Because the cells of hardwood species are thicker and shorter than those of softwood species, the transmitted laser light will be attenuated more and propagated less in hardwood materials, resulting in a smaller emergent laser spot appearing on the hardwood surface. For the same incident light, the length of the emergent laser spot on a hardwood surface is less than half of that on a softwood surface. The aspect ratio of the emergent laser spot on a hardwood surface could be as low as 1.2:1, while that on a softwood surface is around 2:1. The shape of the emergent laser spot is also affected by wood abnormalities, such as pores in hardwood species and rays in radial sections, resulting in the distortion of the emergent laser spot.

For precision measurement, softwood species and planed wood materials are preferable. The small aspect ratio of the emergent laser spot on a hardwood surface, or jagged edges of the reflected laser spot on a roughsawn surface, will impair the anisotropic distribution of the laser light and make it difficult to determine the grain orientation of hardwood species and roughsawn materials by means of laser scanning.

BRIEF SUMMARY OF THE INVENTION

The present inventors have, however, found that wood grain orientation can be satisfactorily determined by means of laser scanning by taking into account the fact that the anisotropic distribution of laser light on a wood surface, which is an indication of the wood grain orientation, can be enhanced by employing a polarizer to separate the emergent laser light from the reflected laser light, and using phase demodulation to eliminate noise from the image.

According to the present invention, a method of determining the grain orientation of a piece of wood comprises the steps of projecting a beam of linearly polarized laser light onto a wood surface to produce an image comprising elliptically polarized emergent laser light and linearly polarized reflected laser light, in addition to non-laser illumination; employing a polarizer to suppress the reflected laser light and a filter to block the non-laser illumination; and capturing, digitizing and processing the image of the emergent laser light to extract the image orientation indicative of the grain orientation.

More Particularly, the Present Inventors Have Found That:

1. The emergent laser light can be separated from the reflected laser light.

When a linearly polarized laser light strikes a wood surface, the reflected laser light will keep its state of polarization for the most part, while the transmitted laser light will be gradually depolarized due to the dielectric anisotropy of wood cells. After passing through sufficient crystalline regions of wood cellulose, the laser light emerging from the wood surface will become elliptically polarized. By employing a polarizer, the emergent laser light, which carries grain orientation information and is mainly elliptically polarized, can be partially separated from the reflected laser light, which is sensitive to wood surface roughness and mostly linearly polarized.

2. The spot of the emergent laser light can be enlarged to its saturation size.

When the laser output is not very high (<1 mW), on a softwood surface, the emergent laser spot is much dimmer but bigger than the reflected laser spot, while on a hardwood surface, the emergent laser spot is close to the reflected laser spot in both brightness and size. With an increase of the laser output (1~30 mW), the reflected laser spot is amplified proportionally, but the emergent laser spot is enlarged gradually to its saturation size. For hardwood species, a bigger emergent laser spot is needed to cope with spot distortion caused by wood abnormalities. By employing a polarizer, the amplified reflected laser spot can be suppressed and the enlarged emergent laser spot can be retained having its saturation size.

3. Laser image orientation can be extracted by one-dimensional phase demodulation.

First, the image of a laser spot or spot-matrix on a wood surface can be transformed into a one-dimensional periodic signal. For the laser spot, the transformation comprises the steps of establishing a polar coordinate system with the pole at the center of the laser spot, and scanning the light intensity of each ray as a function of polar angle. For the laser spot-matrix, the transformation comprises the steps of applying a circular operator to the image, scanning the orientation vector of each pixel of the image, and calculating a histogram of image orientation.

Second, by calculating the real and imaginary part of the second spectrum of the one-dimensional periodic signal, the initial phase, which indicates laser image orientation, can be demodulated from a jagged amplitude, which reflects laser image noise caused by surface roughness, wood abnormalities, and the orientation variation of the wood cells, which are sampled by the laser spot or spot-matrix.

Third, the greater the contrast of the periodic signal, the higher the precision of the phase demodulation. With an increase of the laser output, the signal contrast increases accordingly. Once the signal contrast reaches its maximum, any decrease of the signal contrast may be used as a feedback signal to adjust the laser output for maximizing the signal contrast and increasing the demodulation precision.

Based on the above findings, the present inventors have developed a laser scanning system for wood grain orientation determination. The system includes a polarizing prism for separating the emergent laser light from the reflected laser light, and a function generator for enlarging the emergent laser spot or maximizing the signal contrast, and may employ an algorithm of phase demodulation for signal transformation, phase demodulation, and contrast feedback. The system is capable of extracting wood grain orientation quickly and precisely from laser images with low signal-to-noise ratio, such as the images on the surfaces of hardwood species and roughsawn materials.

BRIEF DESCRIPTION OF THE DRAWINGS

The invention will be more readily understood from the following description of embodiments thereof given, by way of example, with reference to the accompanying drawings, in which.

DESCRIPTION OF THE PREFERRED EMBODIMENTS

Figure 1:
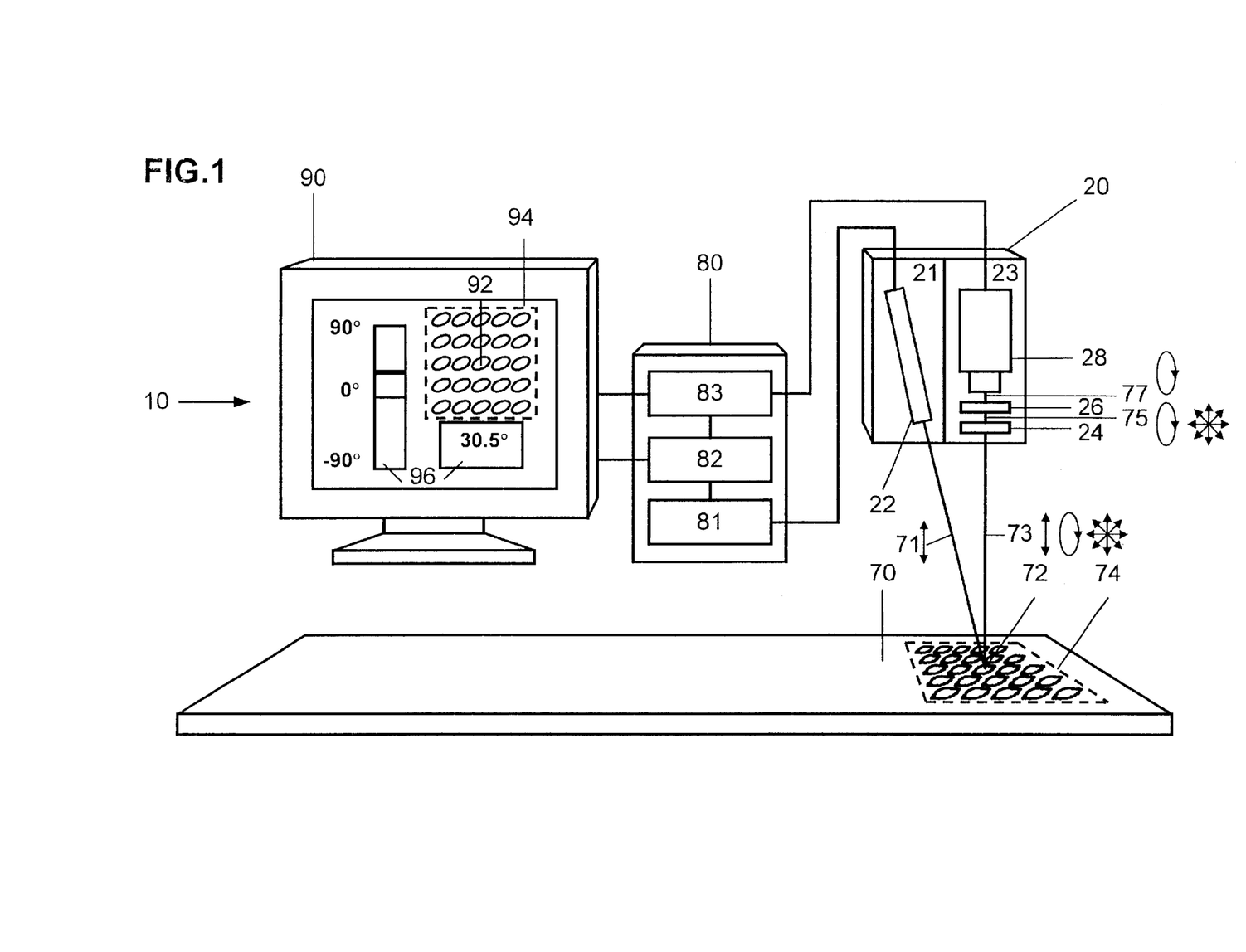
FIG. 1 is a perspective view of a wood grain orientation detecting system according to the present invention.

In FIG. 1 of the accompanying drawings, there is shown a wood grain orientation detecting system indicated generally by reference numeral 10. The hardware of the system 10 comprises two major components, a laser scanner 20 and a controller 80.

The laser scanner 20 comprises a laser projector 21 and a laser detector 23. The laser projector 21 includes a diode laser 22 and other diode laser components, and is designed to project a beam of laser light to form on the surface of a wood panel 70 a light spot 72 or spot-matrix 74. The laser detector 23 includes a polarizing prism 24, an interference filter 26 and a CCD camera 28, and is designed to capture the image of the emergent laser light from the light spot 72 or spot-matrix 74.

The controller 80 is an integrated computer platform and comprises a function generator 81, a computer 82, and an image grabber 83.

The software of the system 10 is a Windows program. It is designed to interface the computer 82 to the function generator 81 and the image grabber 83 to control the laser projector 21 and the laser detector 23, respectively. The software runs under the Windows environment, controls the operation of the system 10, and provides a user-friendly interface on the screen of a monitor 90 with a captured oriented laser image 92 or 94 and a demodulated wood grain orientation 96 displayed.

Figure 2:
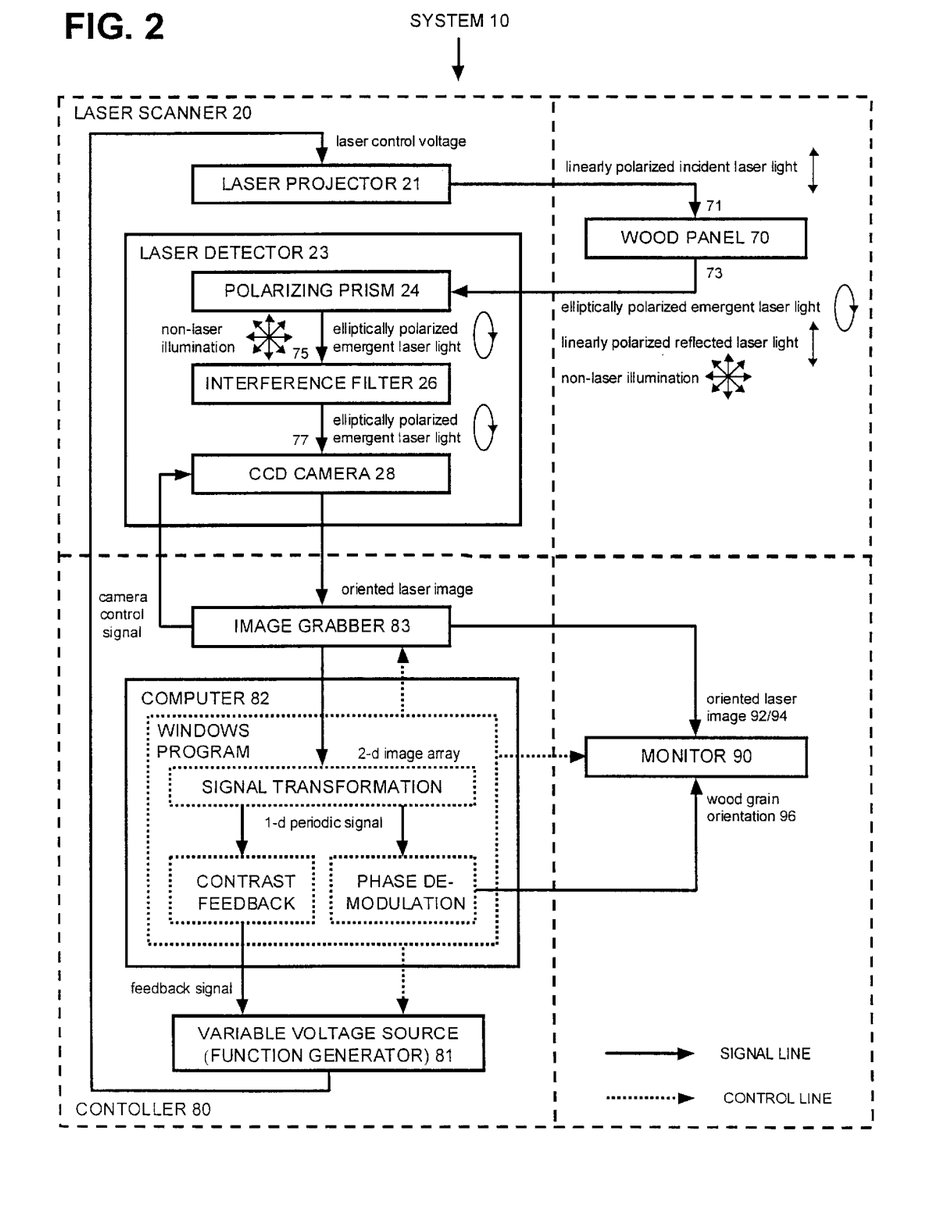
FIG. 2 is a signal flow chart, which diagrammatically illustrates steps associated with operations of the system of FIG. 1.

In operation of the above-described system, as illustrated in FIG. 2, the laser projector 21, under the control of the function generator 81, emits a beam of linearly polarized laser light 71 onto the wood panel 70. In the process of the interaction of the wood material with the laser light, in the manner described above, the light image or spot 72 or spot-matrix 74, consisting of an elliptically polarized emergent laser light and a linearly polarized reflected laser light, in addition to non-laser illumination, is formed on the surface of the wood panel 70.

After light 73, which as shown in FIGS. 1 and 2 is a mixture of linearly polarized reflected laser light, elliptically polarized emergent laser light and non-laser illumination, passes from the light spot 72 or spot-matrix 74 through the polarizing prism 24, which is set to suppress the linearly polarized reflected laser light, thus-separated light 75, which is a mixture of the non-laser illumination and the elliptically polarized emergent light, passes to the interference filter 26, which is set to block non-laser illumination. The elliptically polarized emergent laser light, which is indicated by reference numeral 77, reaches the CCD camera 28, forming an oriented laser image on the CCD array of the CCD camera 28.

The oriented laser image is digitized by and stored in the image grabber 83 in the form of an I×J two-dimensional image array $$G = \begin{bmatrix} g(0,0) & \cdots & g(i,0) & \cdots & g(I-1,0) \\ \vdots & & \vdots & & \vdots \\ g(0,j) & \cdots & g(i,j) & \cdots & g(I-1,j) \\ \vdots & & \vdots & & \vdots \\ g(0,J-1) & \cdots & g(i,J-1) & \cdots & g(I-1,J-1) \end{bmatrix}.$$

g(i,j) is the gray level of the pixel on ith column and jth row of the image. The two-dimensional image array is then sent to the computer 82 for image processing and to the monitor 90 for image display.

The core of the Windows program for image processing is a phase demodulation algorithm, which can be divided into three parts: signal transformation, phase demodulation, and contrast feedback.

The signal transformation for an oriented laser spot 92 includes three steps:
1. Establish a polar coordinate system on the oriented laser image.
2. Search the center of the elongate laser spot as the pole $$x_c = \sum_{i=0}^{I-1} i \cdot \sum_{j=0}^{J-1} g(i,j) \bigg/ \sum_{i=0}^{I-1} \sum_{j=0}^{J-1} g(i,j),$$

$$y_c = \sum_{j=0}^{J-1} j \cdot \sum_{i=0}^{I-1} g(i,j) \bigg/ \sum_{j=0}^{J-1} \sum_{i=0}^{I-1} g(i,j).$$

3. Scan the sum of the gray level of each ray $$G(n) = \sum_{r=0}^{R} g[x_c + r\cos\phi(n), y_c + r\sin\phi(n)]$$

as a function of polar angle $$\phi(n)=2\pi/N,$$

forming a one-dimensional periodic signal. R is the minimum distance between the pole and image edges $$R=\min\{x_c, I-x_c, y_c, J-y_c\}.$$

The signal transformation for an oriented laser spot-matrix 94 includes three steps:
1. Apply a circular operator to the oriented laser image. A simple mask of the circular operator is $$W = \begin{bmatrix} w(-1,-1) & w(0,-1) & w(1,-1) \\ w(-1,0) & w(0,0) & w(1,0) \\ w(-1,1) & w(0,1) & w(1,1) \end{bmatrix} = \begin{bmatrix} -0.464 & 0.000 & 0.464 \\ -0.959 & 0.000 & 0.959 \\ -4.64 & 0.000 & 0.464 \end{bmatrix}.$$

The cross-correlations of the operator mask W with the image array G are $$a_x(i,j) = \sum_{m=-1}^{1} \sum_{n=-1}^{1} w(m,n) \cdot g(i+m, j+n),$$

$$a_y(i,j) = \sum_{m=-1}^{1} \sum_{n=-1}^{1} w(m,n) \cdot g(i+n, j-m).$$

2. Scan the orientation vector of each pixel of the image $$a(i,j) = \sqrt{a_x(i,j)^2 + a_y(i,j)^2},$$

$$\phi(i,j) = tg^{-1}\frac{a_y(i,j)}{a_x(i,j)}.$$

3. Calculate the histogram of the orientation $$G(n) = \left[\sum_{i=0}^{I-1}\sum_{j=0}^{J-1} a(i,j)\right]_{\phi(i,j)=\phi(n)}$$

as a function of image orientation $$\phi(n)=2\pi n/N,$$

forming a one-dimensional periodic signal.

The phase demodulation includes calculating the real and imaginary parts of the second spectrum of the one-dimensional periodic signal G(n)

$$R_2 = \sum_{n=0}^{N-1} G(n)\cos(4\pi n/N),$$

$$I_2 = \sum_{n=0}^{N-1} G(n)\sin(4\pi n/N),$$

and calculating the phase of the spectrum $$\theta = \frac{1}{2} tg^{-1} \frac{I_2}{R_2},$$

as an indication of wood grain orientation, which is sent to the monitor 90 for data display.

The contrast feedback includes calculating the contrast of the one-dimensional periodic signal G(n)

$$\gamma = \frac{G(n)_{max} - G(n)_{min}}{G(n)_{max} + G(n)_{min}},$$

and creating a feedback signal when the signal contrast is decreased due to the variation of the laser output. The feedback signal is sent to a variable voltage source in the form of a function generator 81 to adjust its laser control voltage, which is sent to the laser projector 21 to change its laser output, in a closed-loop operation.

From a signal viewpoint, the light spot 72 or spot-matrix 74, consisting of the emergent and reflected laser light, in addition to non-laser illumination, can be considered as a superposition of a signal (elongate shapes indicating the grain orientation) and noise (jagged edges showing the surface qualities). The signal-to-noise ratio of the image on a hardwood surface, where the signal is weak, or a rough-sawn surface, where the noise is high, is much lower than that on a planed softwood surface. As a result, previous laser scanning systems, which can measure the grain orientation of a planed softwood surface, have been limited by wood species and surface qualities and have hitherto not been reported to perform well for hardwood species and rough-sawn materials.

The system 10 of FIG. 1, however, is capable of improving the signal-to-noise ratio of the image on a wood surface. On the one hand, the combination of the function generator 81 for adjusting the incident laser light and the polarizing prism 24 for suppressing the reflected laser light is used to increase the signal and decrease the noise of the image. On the other hand, the phase demodulation algorithm, which can quickly and precisely extract the laser image orientation, is used to further improve the signal-to-noise ratio of the image. The present method therefore leads to the solution that laser scanning, with its advantages of non-contact, low cost, high flexibility and good performance, can effectively detect the grain orientation not only for planed softwood surfaces, but for hardwood species and roughsawn materials.

The speed of the system 10 is determined by the time required for the image grabbing and processing. It could be higher than 10 data/sec. by using a high speed CCD camera and a high speed image grabber. The precision of the system 10 is determined by the wood species and surface qualities. The maximum standard deviation of measured grain orientation could be as low as 0.1° for planed softwood surfaces and as high as 1° for roughsawn hardwood surfaces.

Embodiments of the laser scanners for laser spot scanning and laser spot sampling are illustrated in FIG. 3~FIG. 6.

Figure 3:
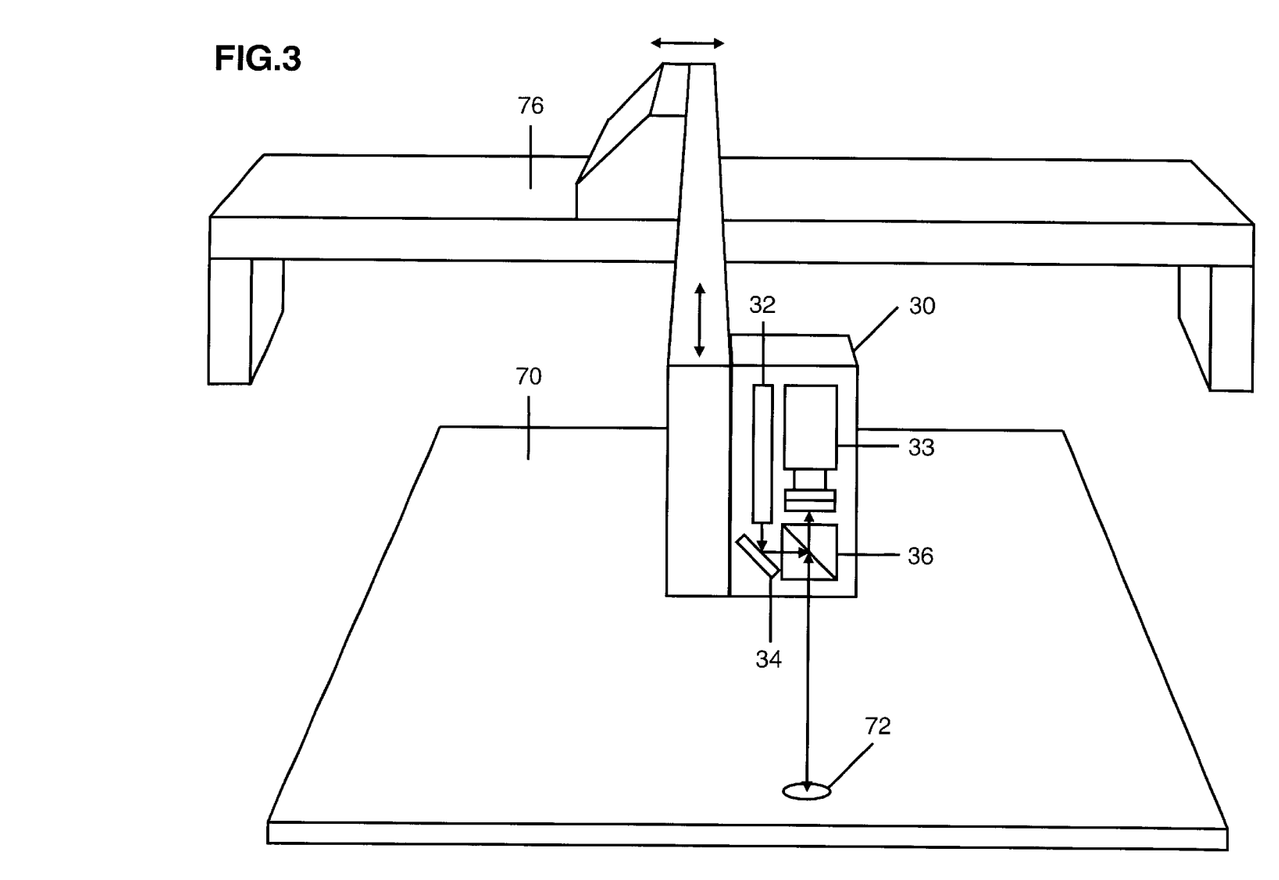
FIG. 3 is a perspective view of a first embodiment of a laser scanner in the system of FIG. 1 for high-precision laser spot scanning.

In FIG. 3, the laser projector of a laser scanner 30 includes a diode laser 32, a diode laser mirror 34 and a diode laser beam splitter 36. The mirror 34 and the beam splitter 36 are used to change the direction of the laser beam to be coaxial to a laser detector 33 to correspondingly decrease the geometric distortion of the light spot 72. The laser scanner 30 is connected to a motorized linear positioning table 76 and moved horizontally and vertically over the wood panel 70 to perform the laser spot scanning.

Figure 4A:
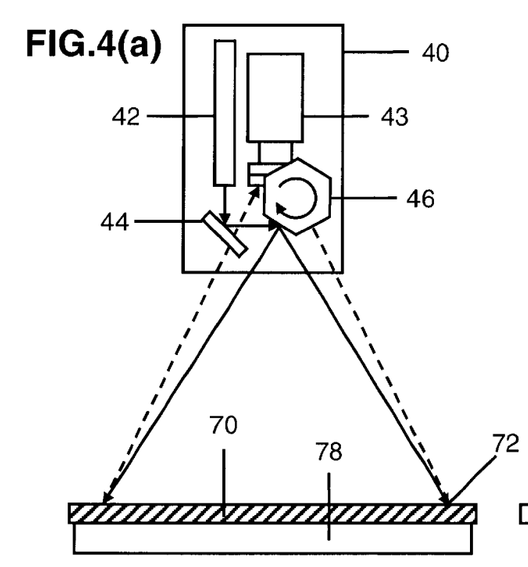
FIGS. 4(a), 4(b) and 4(c) show, respectively, a front view, a side view and a top view of a second embodiment of the laser scanner in the system of FIG. 1 for high-speed laser spot scanning.
Figure 4B:
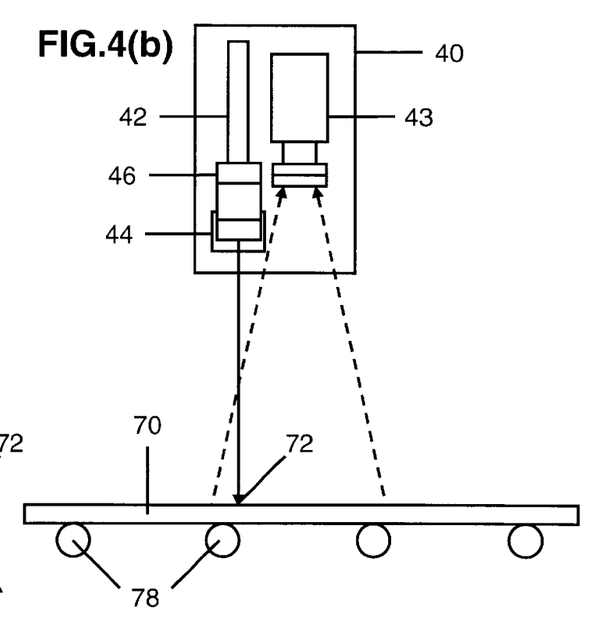
Figure 4C:
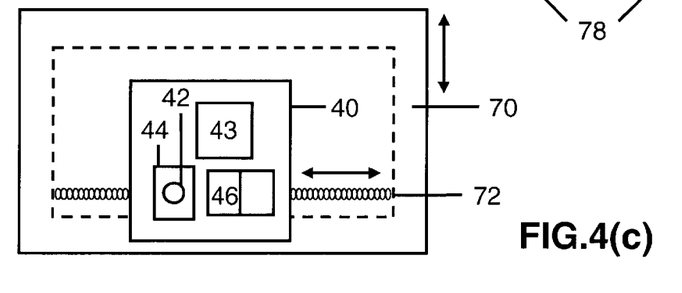

In FIGS. 4(a) to 4(c), the laser projector of a laser scanner 40 includes a diode laser 42, a diode laser mirror 44 and a rotating polygon 46. The laser beam is reflected by the mirror 44 and scanned by the rotating polygon 46, producing the light spot 72 moving on the surface of the wood panel 70 and sensed by a laser detector 43. The wood panel 70 is travelling on the conveyor represented by rollers 78.

Figure 5A:
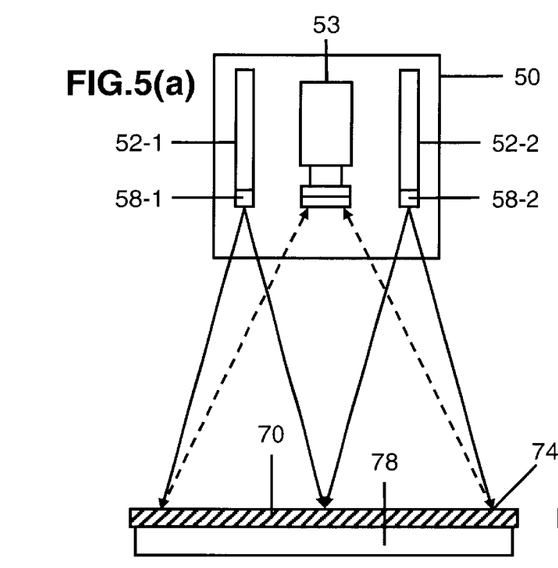
FIGS. 5(a), 5(b) and 5(c) show, respectively, a front view, a side view and a top view of a third embodiment of the laser scanner in the system of FIG. 1 for low-density laser spot sampling.
Figure 5B:
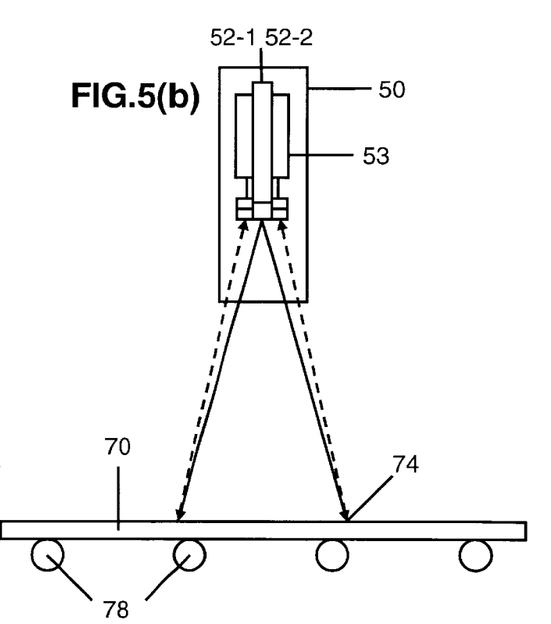
Figure 5C:
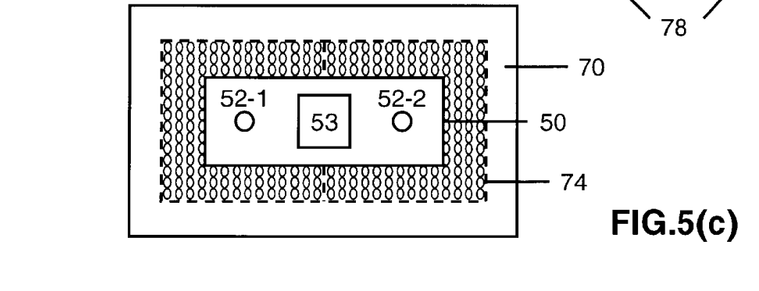

In FIGS. 5(a) to 5(c), the laser projector of a laser scanner 50 includes two diode lasers 52-1 and 52-2 with dot-matrix elements 58-1 and 58-2 attached. The laser projector generates a low-density light spot-matrix 74 on the surface of the wood panel 70 for low-density laser spot sampling. A laser detector 53 is in a low-rate scan mode for capturing the whole image. The wood panel 70 is travelling on the conveyor represented by rollers 78.

Figure 6A:
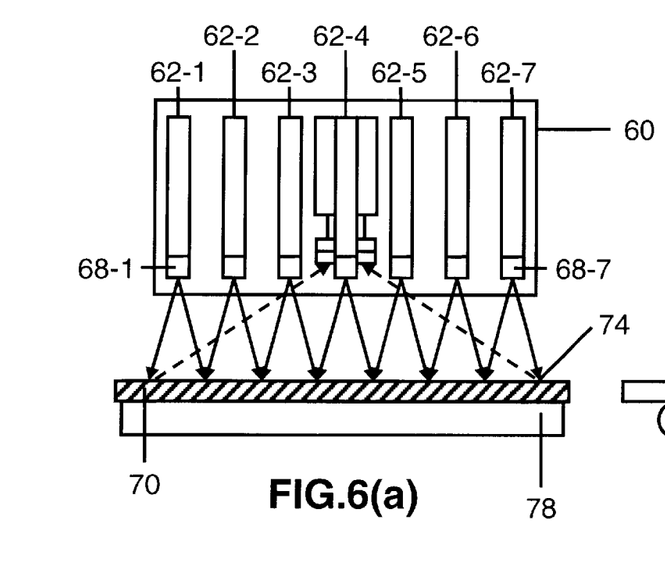
FIGS. 6(a), 6(b) and 6(c) show, respectively, a front view, a side view and a top view of a fourth embodiment of the laser scanner in the system of FIG. 1 for high-density laser spot sampling.
Figure 6B:
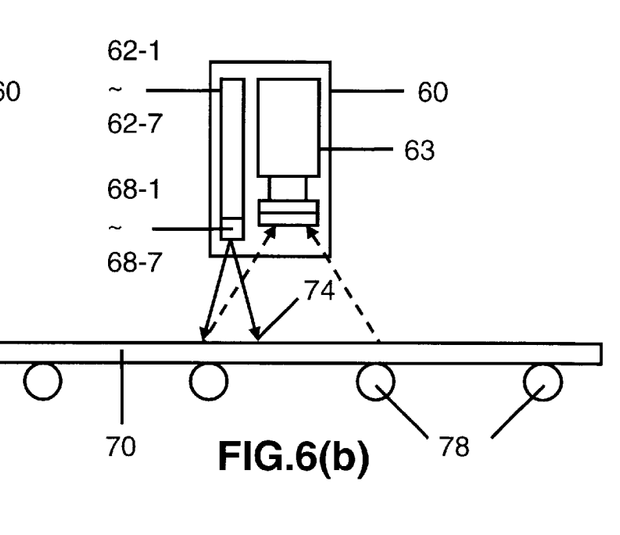
Figure 6C:
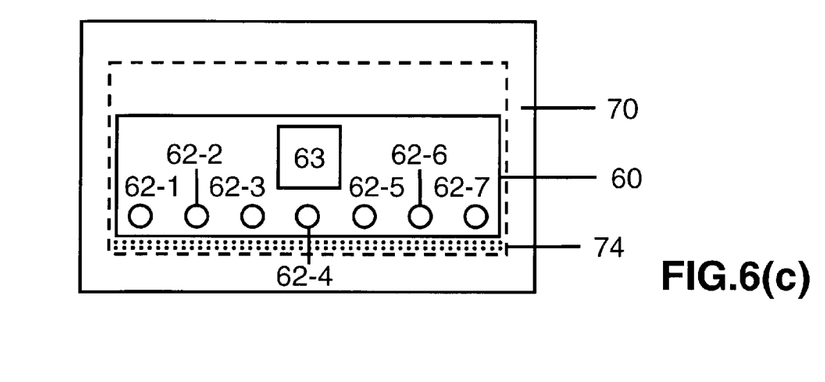

In FIGS. 6(a) to 6(c), the laser projector of a laser scanner 60 includes seven diode lasers 62-1 to 62-7 with dot-matrix elements 68-1 to 68-7 attached. The laser projector generates a high-density light spot-matrix 74 on the surface of the wood panel 70 for high-density laser spot sampling. A laser detector 63 is in a high-rate scan mode for capturing a fourth of the image. The wood panel 70 is travelling on the conveyor represented by rollers 78.

The hardware components of the above-described systems are all commercially available.

The diode laser 22, or any of the diode lasers 32 to 62, is capable of adjusting its laser output and focal point. With a laser output control installed, the diode laser can change its laser output according to an external laser control voltage. To give consideration to adjusting the laser output linearly and enlarging the emergent laser spot, the diode laser is preferably of 30 mW. With the capability of adjusting the focussing lens of the diode laser, the laser spot size on a wood surface, which determines the resolution of the system 10, can be changed from millimeters to centimeters.

While preferred embodiments of the present invention have been described, it will be evident to those skilled in the art that further modifications of the illustrated embodiments are possible without departing from the scope of the invention. For example, it is not essential to install the function generator 81 to control the laser output. A computer I/O board could alternatively be used to provide laser control voltage. Therefore, the scope of the invention is not restricted to the particular embodiments that have been described, but rather includes any modification falling within the following claims.

We claim:

1. A method of determining wood grain orientation, which comprises the steps of:

a) projecting a beam of linearly polarized laser light onto a wood surface to produce a dot-matrix laser image comprising elliptically polarized emergent laser light and linearly polarized reflected laser light;

b) separating the elliptically polarized emergent laser light, which carries grain orientation information, from the linearly polarized reflected laser light, which is sensitive to wood surface roughness, by employing a polarizer;

c) intensifying the elliptically polarized emergent laser light by employing a variable voltage source to increase the linearly polarized incident laser light and a polarizer to suppress the linearly polarized reflected laser light; and d) processing the image of the elliptically polarized emergent laser light, which is an oriented laser image, to determine the wood grain orientation.

2. The method of claim 1, wherein said step b) is used to decrease the noise of the oriented laser image to determine the grain orientation of roughsawn materials.

3. The method of claim 1, wherein said step c) is used to increase the signal of the oriented laser image to determine the grain orientation of hardwood species.

4. A method as claimed in claim 1, wherein step d) comprises signal transformation, phase demodulation and contrast feedback to control the linearly polarized laser light projected onto the wood surface.

5. The method of claim 4, in which the image comprises an elongate laser spot and said signal transformation includes establishing a polar coordinate system on the spot; searching the center of the spot as the pole; and scanning the sum of the gray level of each ray as a function of polar angle to form a one-dimensional periodic signal for phase demodulation and contrast feedback.

6. The method of claim 5, which said phase demodulation includes calculating the phase of the second spectrum of said one-dimensional periodic signal as an indication of the wood grain orientation.

7. The method of claim 5, in which said contrast feedback includes calculating the contrast of said one-dimensional periodic signal, creating a feedback signal when the signal contrast is decreased due to the variation of the laser output, and sending the feedback signal to the variable voltage source to adjust its laser control voltage, which is sent to the diode laser to change its laser output, in a closed-loop operation, said contrast feedback being used to maximize the signal contrast to increase the precision of said phase demodulation.

8. The method of claim 4, in which the image comprises an oriented laser spot-matrix and said signal transformation includes applying a circular operator to the image; scanning the orientation vector of each pixel of the image; and calculating a histogram of the orientation vector as a function of image orientation to form a one-dimensional periodic signal for phase demodulation and contrast feedback.

9. The method of claim 9, in which said phase demodulation includes calculating the phase of the second spectrum of said one-dimensional periodic signal as an indication of the wood grain orientation.

10. The method of claim 8, which said contrast feedback includes calculating the contrast of said one-dimensional periodic signal, creating a feedback signal when the signal contrast is decreased due to the variation of the laser output, and sending the feedback signal to the variable voltage source to adjust its laser control voltage, which is sent to the diode laser to change its laser output, in a closed-loop operation, said contrast feedback being used to maximize the signal contrast to increase the precision of said phase demodulation.

11. A method of determining wood grain orientation, which comprises the steps of:
   a) projecting a beam of linearly polarized laser light onto a wood surface to emit from the surface elliptically polarized emergent laser light and linearly polarized reflected laser light;
   b) employing a polarizer to at least partially separate the elliptically polarized emergent laser light from the linearly polarized reflected laser light; and
   c) processing the thus-separated elliptically polarized emergent laser light to provide an indication of the wood grain orientation.

12. The method of claim 11, in which step c) includes producing a feedback signal, and employing the feedback signal to adjust the beam of linearly polarized light projected onto the wood surface so as to increase the elliptically polarized emergent laser light.

13. The method of claim 12, which includes employing the feedback signal to adjust the intensity of the beam of linearly polarized light.

14. The method of claim 12, which includes employing the feedback signal to adjust a spot formed on the wood surface by the elliptically polarized light to its saturation size.

15. The method of claim 11, wherein step c) comprises forming from the separated elliptically polarized laser light an oriented laser image, transforming a signal representing the oriented laser image, which is a two-dimensional image, into a one-dimensional periodic signal, and employing phase demodulation to calculate the phase of the second spectrum of the one-dimensional periodic signal as an indication of the wood grain orientation.

16. The method of claim which includes producing a feedback signal corresponding to the contrast of the one-dimensional periodical signal and employing the feedback signal to control the beam of polarized light projected onto the wood surface.

17. The method of claim 11, in which step a) comprises forming on the wood surface a dot-matrix image.

18. The method of claim 17, wherein step c) comprises forming an oriented two-dimensional image of the separated elliptically polarized emergent laser light, transforming the oriented two-dimensional image with a one-dimensional periodic signal by establishing a polar coordinate system with its pole at the center of the oriented two-dimensional image and scanning the light intensity of rays forming the oriented two-dimensional image as a function of the polar angle.

19. The method of claim 11, which includes calculating the contrast of the one-dimensional periodic signal, creating a corresponding feedback signal and employing the feedback signal to control adjustment of the beam of linearly polarized laser light.

20. The method of claim 11, wherein step c) includes forming an oriented two-dimensional image of the separated elliptically polarized emergent laser light, applying a circular operator to the oriented two-dimensional image, and scanning the orientation vector of each pixel of the oriented two-dimensional image.

21. The method of claim 11, including adjusting the beam of linearly polarized laser light so as to increase the elliptically polarized emergent laser light.

22. Apparatus for determining wood grain orientation, comprising:
   a laser scanner,
   said laser scanner comprising a laser projector for projecting a beam of laser light to form on a wood surface a laser dot-matrix image comprising elliptically polarized emergent laser light, linearly polarized reflected laser light and non-laser illumination;
   a laser detector for capturing the image of the elliptically polarized emergent laser light; and
   a controller,
   said controller comprising a variable voltage source for controlling said laser projector.

23. Apparatus according to claim 22, wherein said laser projector comprises a pair of diode lasers and dot-matrix elements attached to said diode lasers for creating a low-density laser dot-matrix.

24. Apparatus according to claim 22, wherein said laser projector comprises a plurality of diode lasers and dot-matrix elements attached to said diode lasers for creating a high-density laser dot-matrix.

25. Apparatus according to claim 22, wherein said laser detector comprises a polarizer for suppressing the linearly polarized reflected laser light, and a camera aligned with said polarizer for capturing the image of the elliptically polarized emergent laser light.

26. Apparatus for determining wood grain orientation, comprising:
- a laser scanner for projecting linearly polarized light onto a wood surface to form an image on the wood surface;
- a laser detector for detecting light from the image;
- said laser detector including a polarizer for separating elliptically polarized emergent laser light from linearly polarized reflected laser light; and
- a processor connected to the laser detector for providing an indication of the wood grain orientation in accordance with the separated elliptically polarized emergent light.

27. Apparatus claimed in claim 26, wherein a variable voltage source controls said laser scanner.

28. Apparatus as claimed in claim 27, wherein said variable voltage source is controlled by a feedback signal from said processor.

29. Apparatus as claimed in claim 26, wherein said laser detector forms an oriented two-dimensional image of the separated elliptically polarized emergent light, and said processor is programmed to transform the oriented two-dimensional image into a one-dimensional periodic signal and to calculate the phase of the second spectrum of the one-dimensional periodic signal.

30. Apparatus as claimed in claim 29, wherein said processor is programmed to produce a feedback signal corresponding to the contrast of the one-dimensional signal, said light scanner including a variable voltage source responsive to said feedback signal and a laser adjustable by said variable voltage source to adjust said linearly polarized laser light in accordance with the feedback signal.

31. Apparatus as claimed in claim 29, wherein said laser detector includes a CCD camera for capturing the oriented two-dimensional image.

32. Apparatus as claimed in claim 26, wherein said laser scanner comprises a plurality of lasers with a plurality of dot-matrix elements for forming a dot-matrix image on the wood surface.

* * * * *